United States Patent
Copland et al.

(10) Patent No.: US 12,349,971 B2
(45) Date of Patent: Jul. 8, 2025

(54) METHOD AND SYSTEM FOR MAKING OPTICAL MEASUREMENT OF EYE

(71) Applicant: AMO Development, LLC, Irvine, CA (US)

(72) Inventors: Richard J. Copland, Albuquerque, NM (US); Daniel R. Neal, Tijeras, NM (US); Thomas D. Raymond, Edgewood, NM (US)

(73) Assignee: AMO Development, LLC, Irvine, CA (US)

( * ) Notice: Subject to any disclaimer, the term of this patent is extended or adjusted under 35 U.S.C. 154(b) by 598 days.

(21) Appl. No.: 17/595,561

(22) PCT Filed: May 20, 2020

(86) PCT No.: PCT/IB2020/054793
§ 371 (c)(1),
(2) Date: Nov. 18, 2021

(87) PCT Pub. No.: WO2020/234805
PCT Pub. Date: Nov. 26, 2020

(65) Prior Publication Data
US 2022/0225875 A1    Jul. 21, 2022

Related U.S. Application Data

(60) Provisional application No. 62/852,170, filed on May 23, 2019.

(51) Int. Cl.
*A61B 3/10* (2006.01)
*A61B 3/103* (2006.01)
(Continued)

(52) U.S. Cl.
CPC ............ *A61B 3/1015* (2013.01); *A61B 3/103* (2013.01); *A61B 3/1216* (2013.01); *A61B 3/152* (2013.01)

(58) Field of Classification Search
CPC ..... A61B 3/1015; A61B 3/103; A61B 3/1216; A61B 3/152; A61B 3/12; A61F 2/1654
(Continued)

(56) References Cited

U.S. PATENT DOCUMENTS 6,550,917 B1    4/2003  Neal et al.
7,122,774 B2    10/2006 Topa
(Continued)

FOREIGN PATENT DOCUMENTS

JP    2012075647 A       4/2012
JP    2017213124 A    *  12/2017

OTHER PUBLICATIONS

Gutman A.S., et al., "Optical testing of bifocal Diffractive-Refractive Intraocular Lenses using shack-Hartmann Wavefront Sensor." Proceedings of SPIE 7718, Optical Micro- and Nanometrology III, 77181P (May 14, 2010), (https://doi.org/10.1117/12.854484).

*Primary Examiner* — Mohammed A Hasan

(57) ABSTRACT

A method and device: pass a probe beam to the retina of an eye through a refractive region of a combined diffractive-re-fractive intraocular lens (IOL) which is implanted into the eye; provide light returned from the retina to a wavefront sensor which includes a detector array and images the returned light onto the detector array to produce a first set of light spots which returned from the retina through the refractive region of the combined diffractive-refractive IOL and a second set of light spots which returned from the retina through a diffractive region of the combined diffractive-refractive IOL; select a first region of the detector array which includes at least some of the first set of light spots and excludes the second set of light spots; and determines a refraction of the eye with the combined diffractive-refractive IOL implanted therein using only data from the first set of light spots.

18 Claims, 17 Drawing Sheets

(51) Int. Cl.
*A61B 3/12* (2006.01)
*A61B 3/15* (2006.01)

(58) Field of Classification Search
USPC .......................................................... 351/205
See application file for complete search history.

(56) References Cited

U.S. PATENT DOCUMENTS

| | | | |
|---|---|---|---|
| 7,494,220 B2 | 2/2009 | Copland | |
| 7,988,293 B2 | 8/2011 | Raymond et al. | |
| 8,622,546 B2 | 1/2014 | Farrer et al. | |
| 8,777,413 B2 | 7/2014 | Zhou et al. | |
| 9,462,937 B2 | 10/2016 | Ohta | |
| 2003/0038921 A1* | 2/2003 | Neal | G01M 11/0264 351/212 |
| 2004/0041978 A1 | 3/2004 | Neal et al. | |
| 2007/0070292 A1 | 3/2007 | Liang | |
| 2009/0002631 A1 | 1/2009 | Campbell et al. | |
| 2009/0185132 A1* | 7/2009 | Raymond | G01M 11/0292 356/124 |
| 2010/0123873 A1 | 5/2010 | Raymond et al. | |
| 2011/0149239 A1* | 6/2011 | Neal | A61B 3/103 351/205 |
| 2011/0273669 A1* | 11/2011 | Abitbol | A61B 3/1015 351/212 |
| 2012/0314187 A1* | 12/2012 | Farrer | A61B 3/1015 351/221 |
| 2015/0320310 A1 | 11/2015 | Zhou et al. | |
| 2016/0000316 A1* | 1/2016 | Copland | A61B 3/103 351/221 |
| 2018/0242840 A1 | 8/2018 | Copland | |
| 2020/0054213 A1* | 2/2020 | Copland | A61B 3/12 |

* cited by examiner

METHOD AND SYSTEM FOR MAKING OPTICAL MEASUREMENT OF EYE

CROSS REFERENCE TO RELATED APPLICATIONS

This application is a U.S. national stage of and claims the benefit under 35 U.S.C. § 371 of International Patent Application No. PCT/IB2020/054793, filed May 20, 2020, which claims priority to U.S. Provisional Patent Application No. 62/852,170, filed on May 23, 2019, the entire contents of which are hereby incorporated by reference in their entirety.

BACKGROUND AND SUMMARY

Field

This invention pertains to systems and methods for making optical measurements of eyes, and more specifically to a system and method for making optical measurements of an eye with an implanted combined diffractive-refractive intraocular lens.

Description

A "normal" lens includes at least one curved surface which is focuses light. This may be referred to as a refractive optical element.

One can also make a flat optic with (typically etched) diffraction features formed in a surface which focuses light by constructive interference. Such a device is referred to as a diffractive optical element.

FIG. 1 is a cross-section view of an example of a diffractive optical element 1. Diffractive optical element 1 has a plurality of diffraction features 2 formed in a surface thereof. Here, diffraction features 2 may be a series of concentric rings with triangular cross-sections or profiles.

Typically most of the light will pass straight through diffractive optical element 1, as shown in FIG. 1. But some fraction of the light will be diffracted by the diffraction features 2 and will form a diffractive focal spot 3, as indicated by the dashed lines. Typically, between 10 and 30% of the light energy which impinges on diffractive optical element 1 is diverted into diffractive focal spot 3.

In diffractive optical element 1, the spacing between the rings, the angles of the triangular cross-sections, whether the triangular cross-sections are adjacent to or touch each other, or if there are flat spots in between them, are all design parameters which may be selected according to the desired characteristics of diffractive optical element 1.

In addition to refractive optical elements and diffractive optical elements, one can produce an optical element which includes both one or more diffractive regions and one or more separate refractive regions. Such an element may be referred to as a combined diffractive-refractive optical element.

Combined diffractive-refractive intraocular lenses (IOLs) have become a popular option for implantation into an eye when the natural lens has become compromised and in need of replacement. Herein, a combined diffractive-refractive IOL refers to an IOL which includes at least one refractive region which focuses light with a curved surface, and one or more separate diffractive regions which focus light by constructive interference produced by features such as rings that are etched or otherwise fabricated into the optical element.

FIGS. 2A and 2B illustrate an example of a combined diffractive-refractive IOL 20. Combined diffractive-refractive IOL 20 includes a central refractive region 21 and a peripheral diffractive region 22.

FIG. 2A illustrates an example where light rays from very far away impinge on combined diffractive-refractive IOL 20. In this case, parallel rays of light from very far away which pass through the central refractive region 21 are focused at a focal point 24A on the retina. Meanwhile, the parallel rays of light from very far away which pass through peripheral diffractive region 22 are focused at a diffractive focal spot 24B which is located in front of the retina. When that light eventually gets to the retina, it is a fuzzy blob and the brain ignores it.

FIG. 2A illustrates an example where light rays from a point 5 which is located relatively near to the eye impinge on combined diffractive-refractive IOL 20. In this case, at least some portion of the light rays which pass through peripheral diffractive region 22 are focused at a diffractive focal spot 24C which is located at the retina and may be interpreted by the brain. Meanwhile, light rays from point 5 which pass through central refractive region 21 focus at a focal point 24D behind the retina. This light appears as a fuzzy unfocused blob at the retina and is basically ignored by the brain.

Thus combined diffractive-refractive IOL 20 may provide both near vision and distance vision ability to someone into whose eye it is implanted.

After implantation of an IOL, it is desirable to objectively measure the patient's post-operative refraction to assess their vision. However, when a combined diffractive-refractive IOL is implanted, this becomes problematic.

Therefore, it would be desirable to provide a system and method which can measure a refractive power of an eye which has a combined diffractive-refractive IOL implanted therein.

In one aspect of the invention, a method comprises: passing a probe beam to the retina of an eye through a combined diffractive-refractive intraocular lens which is implanted into the eye; providing light returned from the retina to a wavefront sensor which includes a detector array; the wavefront sensor imaging the returned light onto the detector array to produce a first set of light spots on the detector array which returned from the retina through the refractive region of the combined diffractive-refractive intraocular lens and to produce a second set of light spots on the detector array which returned from the retina through at least one diffractive region of the combined diffractive-refractive intraocular lens; selecting a first region of the detector array which includes at least some of the first set of light spots returned from the retina through a refractive region of the combined diffractive-refractive intraocular lens and which excludes the second set of light spots returned from the retina through the at least one diffractive region of the combined diffractive-refractive intraocular lens; a processor receiving from the detector array at least a first set of wavefront data in response to the first set light spots in the first region of the detector array; and the processor determining a refraction of the eye with the combined diffractive-refractive intraocular lens implanted therein using only the first set of wavefront data from the first set light spots in the first region.

In another aspect of the invention, a device comprises: a light source configured to produce a probe beam; optics configured to pass the probe beam to the retina of an eye through a combined diffractive-refractive intraocular lens which is implanted into the eye; a detector array; a light spot generator adapted to receive light returned from the retina and in response thereto to produce on the detector array a first set of light spots which returned from the retina through a refractive region of the combined diffractive-refractive intraocular lens and a second set of light spots on the detector array which returned from the retina through at least one diffractive region of the combined diffractive-refractive intraocular lens; and a processor. The processor is configured to: receive from the detector array at least a first set of wavefront data in response to a first set light spots in a first region of the detector array returned from the retina through the refractive region of the combined diffractive-refractive intraocular lens, wherein the first region excludes the second set of light spots returned from the retina through the at least one diffractive region of the combined diffractive-refractive intraocular lens, and determine a refraction of the eye with the combined diffractive-refractive intraocular lens implanted therein using only the first set of wavefront data from the first set light spots in the first region.

DETAILED DESCRIPTION

Methods and systems for locating valid light spots as described below can be employed in a variety of different measurement instruments. Exemplary embodiments will be described in some detail below so as to illustrate various aspects and advantages of these methods. However, it should be understood that the principles involved in these method can be employed in a variety of other measurement instruments which employ light spots to produce data.

Figure 1:
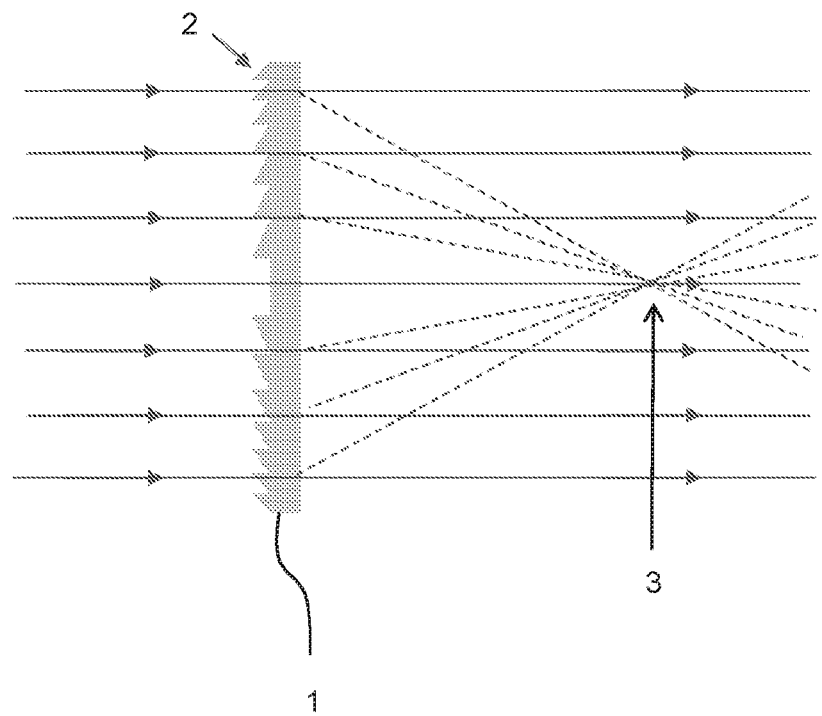
FIG. 1 is a cross-section view of an example of a diffractive optical element.
Figure 2A:
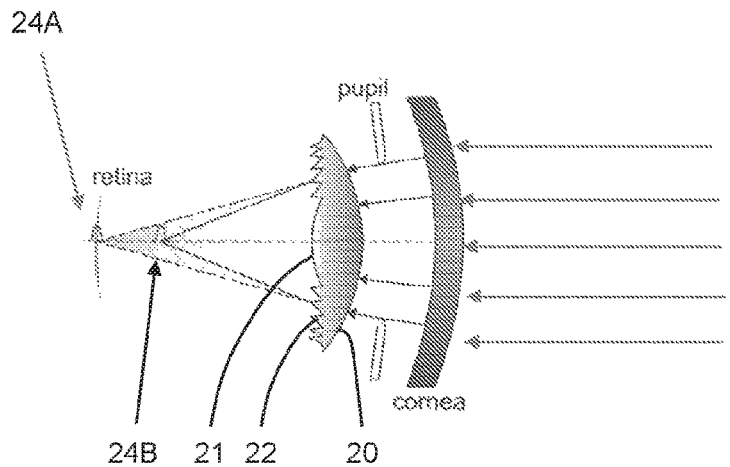
FIGS. 2A and 2B illustrate an example of a combined diffractive-refractive intraocular lens (IOL).
Figure 2B:
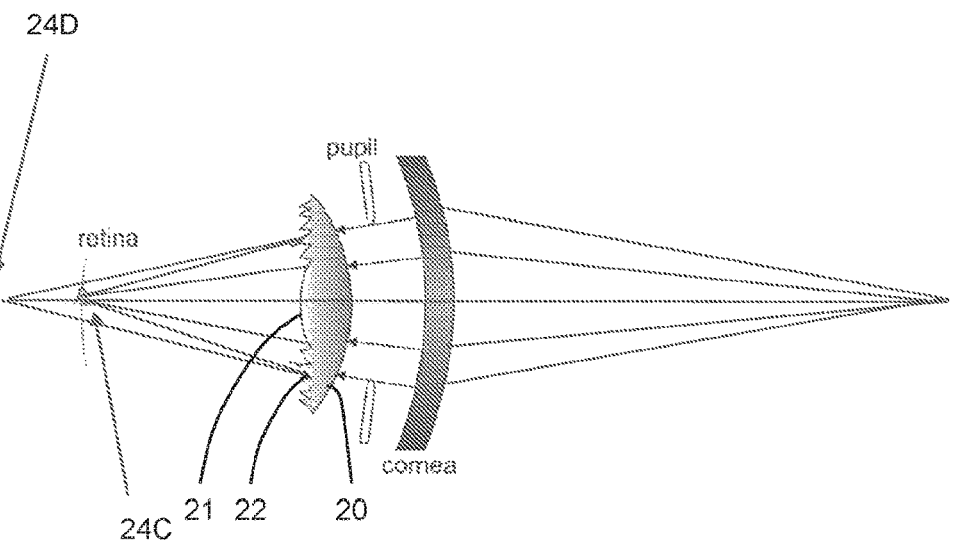
Figure 3:
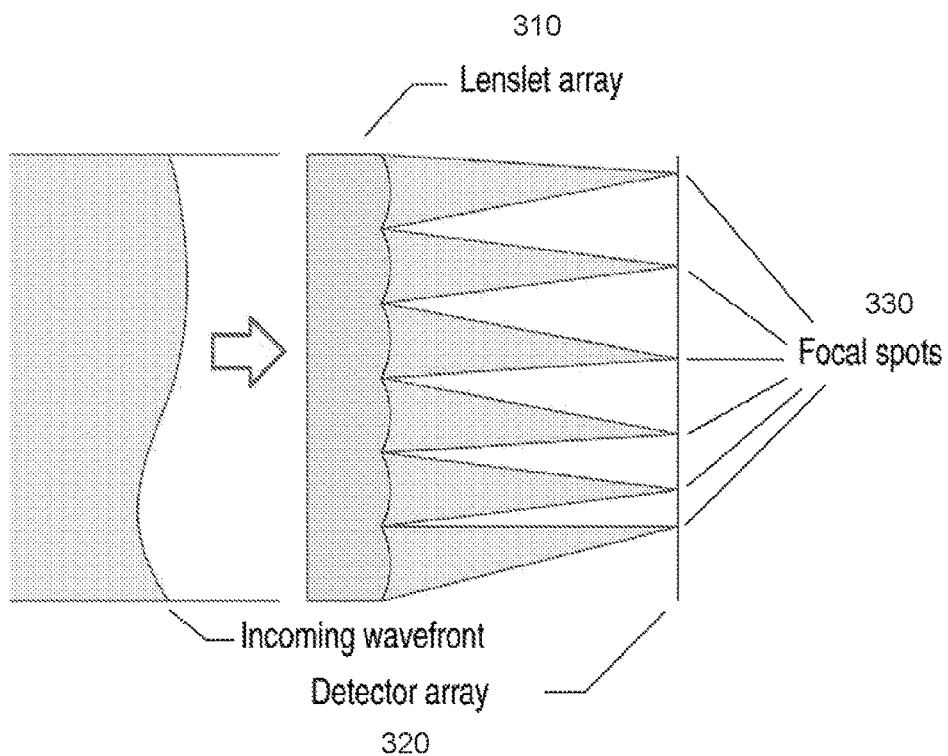
FIG. 3 illustrates some principal elements of a basic configuration of a Shack-Hartmann wavefront sensor.

FIG. 3 illustrates some principal elements of a basic configuration of a Shack-Hartmann wavefront sensor 300. Shack-Hartmann wavefront sensor 300 comprises a micro-optic lenslet array 310 and an optical detector 320. Typically, the optical detector 320 comprises a detector array or pixel array, for example, a charge-coupled device (CCD) camera or CMOS array.

The lenslets of lenslet array 310 dissect an incoming wavefront and create a pattern of light spots 330 that fall onto optical detector 320. That is, lenslet array 310 operates as light spot generator for optical detector (e.g., a detector array) 320. In one typical embodiment, lenslet array 310 includes hundreds or thousands of lenslets, each on the size scale of a hundred microns. Meanwhile, detector array 320 typically comprises many pixels (e.g., about 400 pixels) for each lenslet in lenslet array 310. Typically Shack-Hartmann sensor 300 is assembled such that the detector array 320 lies in the focal plane of lenslet array 310.

Shack-Hartmann wavefront sensor 300 uses the fact that light travels in a straight line to measure the wavefront of light. By sensing the locations of light spots 330, the propagation vector of the sampled light can be calculated for each lenslet of lenslet array 310. The wavefront of the received light can be reconstructed from these vectors.

To better understand one or more aspects of this invention, it is worthwhile to discuss the operation of Shack-Hartmann wavefront sensor 300 in more detail. However, embodiments of the present invention may extend to other types of wavefront sensors.

In the case of Shack-Hartmann wavefront sensor 300, some optical system is employed to deliver a wavefront onto the lenslet array 310, which samples the wavefront over the tiny regions of each lenslet. Beneficially, the lenslets are much smaller than the wavefront variation. For the purposes of this discussion, we define "isoplanatic" as the condition where the wavefront is well approximated by a plane wave over an area the size of a lenslet. In that case, the wavefront is preferably isoplanatic over the sampled region. When optical detector 320—hereafter referred to more specifically as "detector array 320"—is in the focal plane of lenslet array 310, each lenslet will create a light spot on detector array 320. The locations of these light spots reveal the average of the wavefront slopes across each region. That is, the shift in the location of a light spot is proportional to the average of the slope of the wavefront over the region sampled by the corresponding lenslet that produced the light spot. Software may compute the shift in each light spot.

In a typical operation, a reference beam (e.g., a plane wave) is first imaged onto lenslet array 310 and the locations of the resultant light spots ("reference locations") on detector array 320 is recorded. Then, a wavefront of interest is imaged onto lenslet array 310, and the locations of the light spots on detector array 320 produced by the wavefront of interest are recorded and compared against the reference locations.

FIGS. 4A-E illustrate a reference beam and a wavefront of interest being imaged onto a detector array of a wavefront sensor. This idealization shows the process of measuring a spherical wave with a wavefront sensor with just 16 lenslets.

Figure 4A:
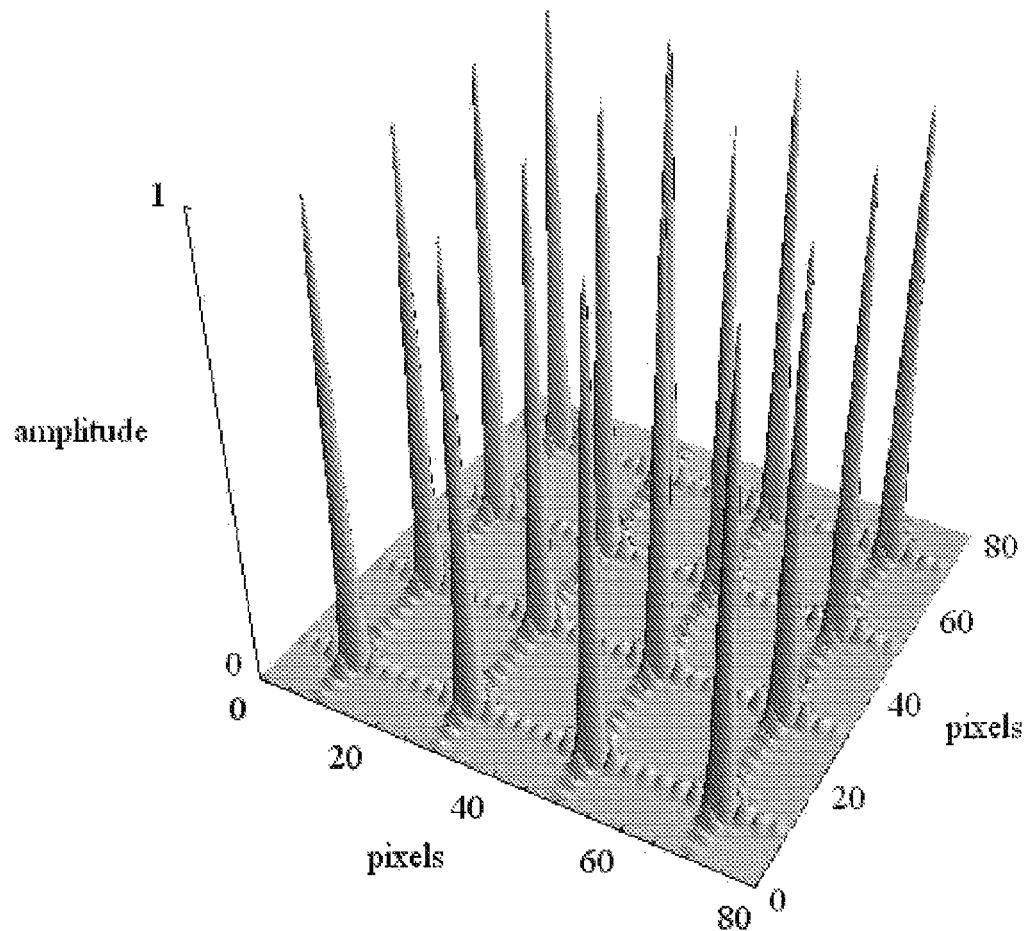
FIGS. 4A, 4B, 4C, 4D and 4E illustrate a reference beam and a wavefront of interest being imaged onto a detector array of a wavefront sensor.
Figure 4B:
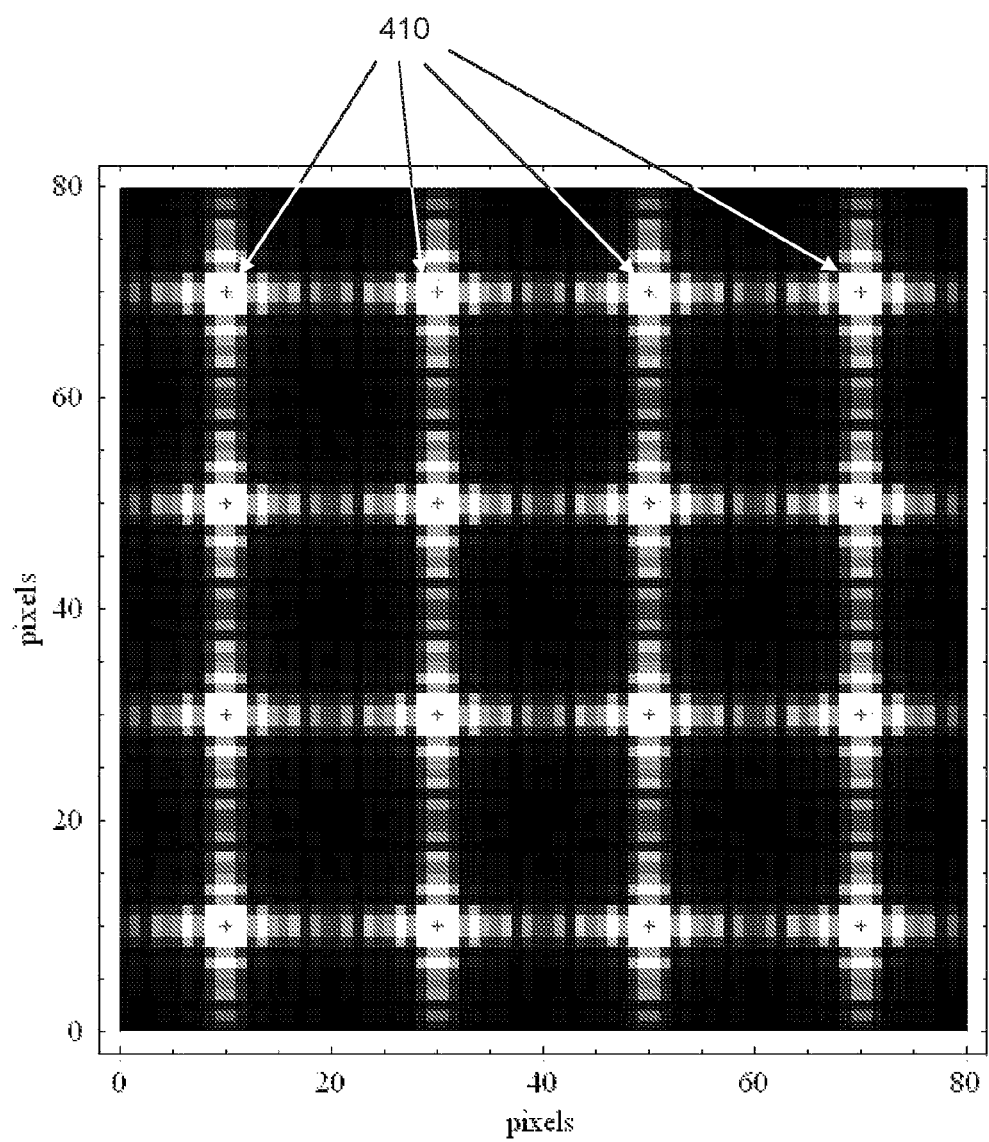
Figure 4C:
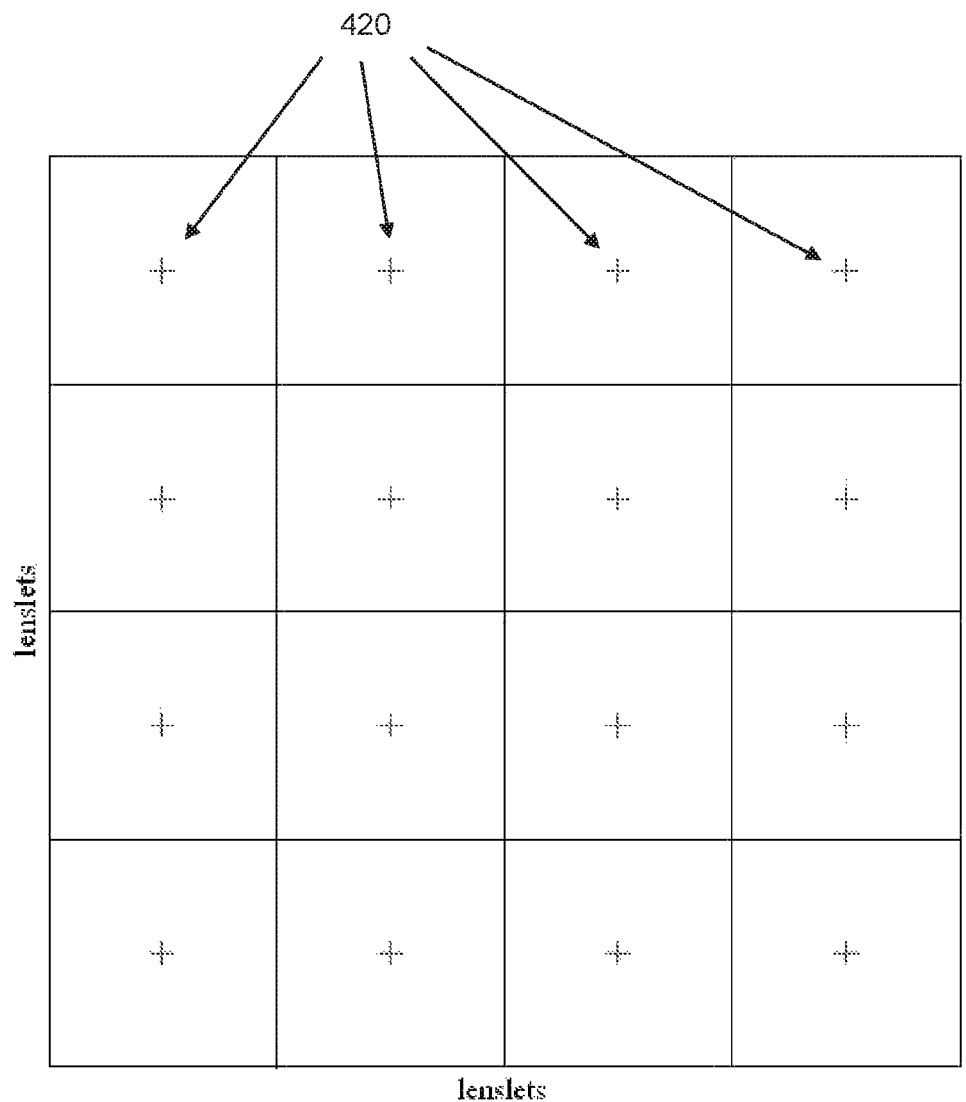

The first step, as represented by the FIGS. 4A-4C, is to measure a plane wave and measure the corresponding series of light spot locations 410 which are used as reference locations 420. For the plane wave, each lenslet of lenslet array 310 produces one light spot on a location 410 within a corresponding Area of Interest (AOI) of detector array 320 that lies beneath that lenslet.

Figure 4D:
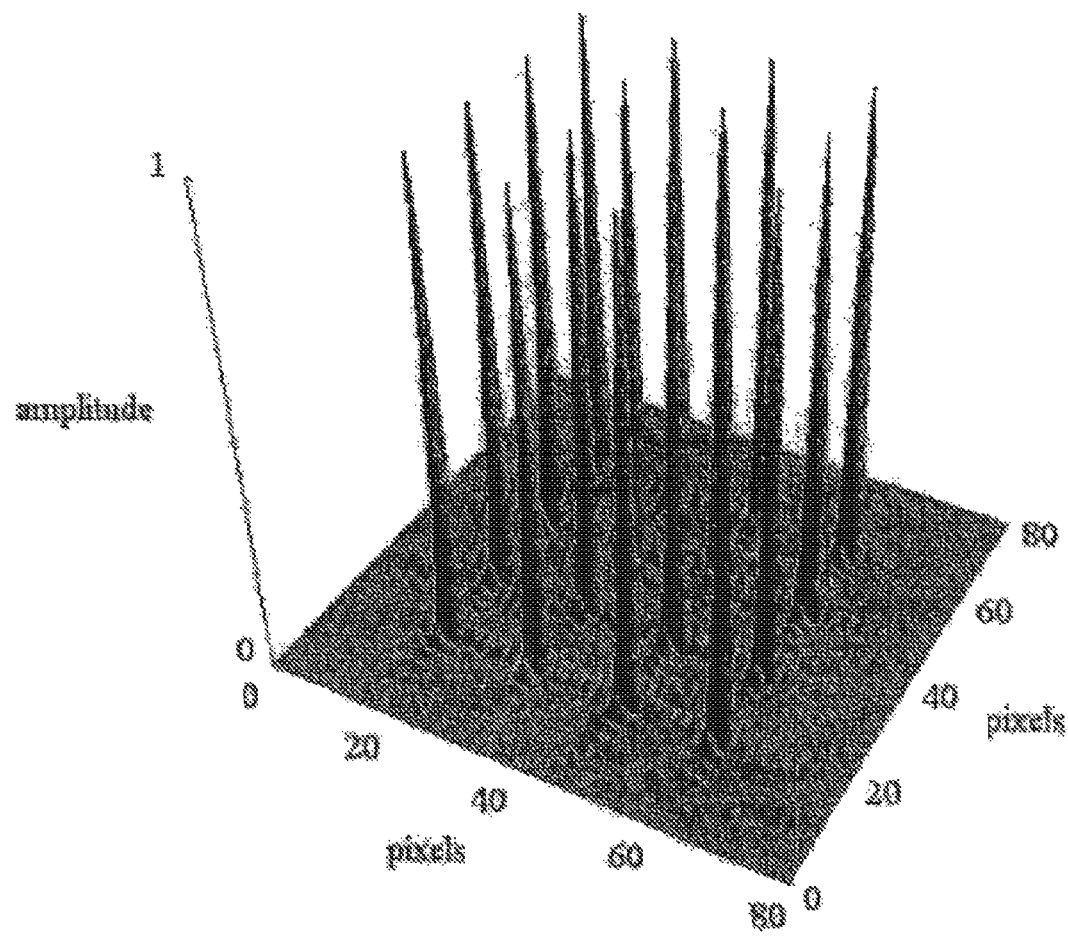
Figure 4E:
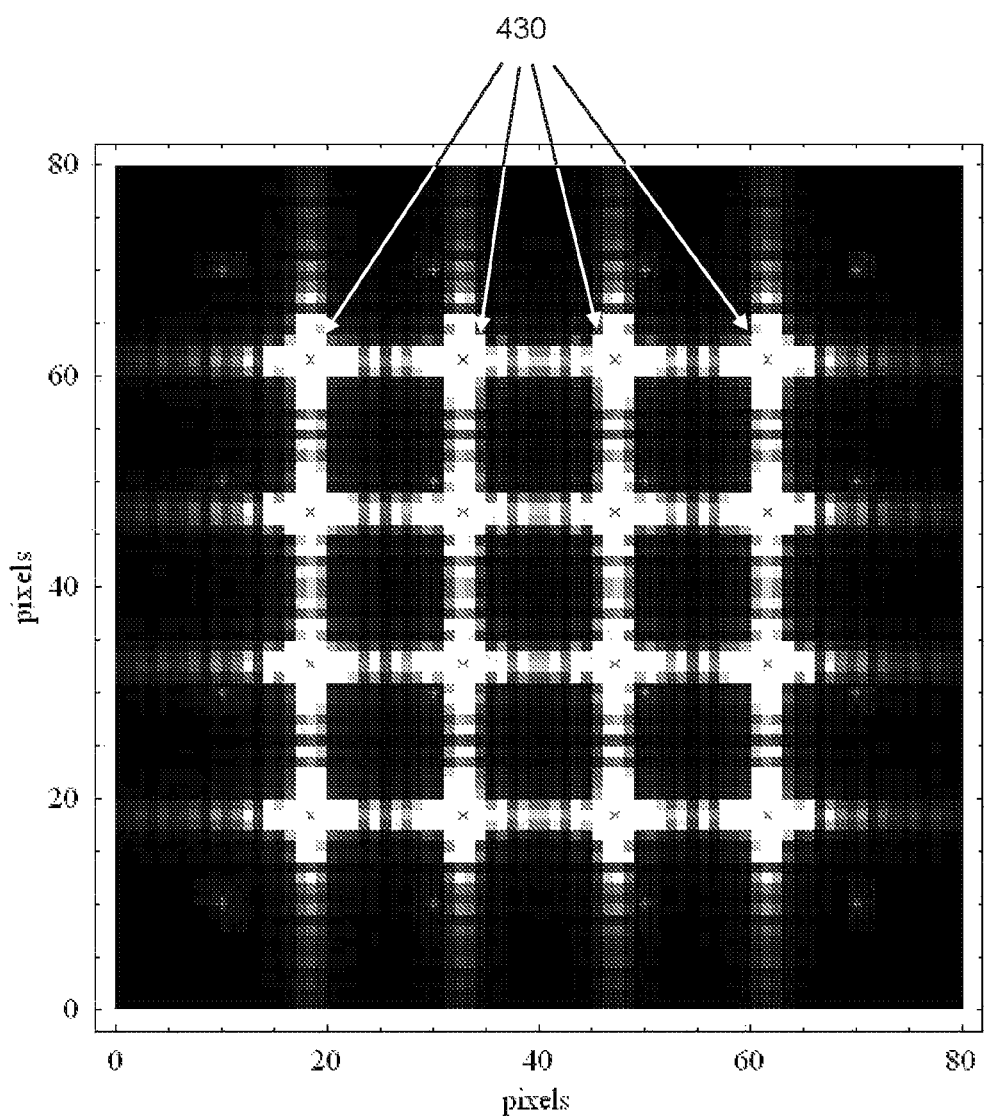

The next step, as depicted in FIGS. 4D-4R, is to introduce a wavefront of interest and determine the shifts in the locations 440 of the light spots 430 from their reference locations 420.

Where the isoplanatic condition is satisfied and where the light spot shift is consistent with the small angle approximation of Fresnel, then the light spot shift is exactly proportional to the average of the wavefront slope over the lenslet. The incident wavefront is then reconstructed from the measurements of the average of the slopes for the hundreds or thousands of lenslets in the lenslet array.

Further details regarding the construction and operation of a Shack-Hartmann wavefront sensor and a system for measuring aberrations in an eye using the Shack-Hartman wavefront sensor are described in U.S. Pat. No. 7,122,774, issued on 17 Oct. 2006 to Daniel R. Neal et al., the entirety of which is hereby incorporated by reference for all purposes as if fully set forth herein.

One important application for Shack-Hartmann wavefront sensors is in the field of ophthalmic aberrometry. In common practice, a measurement instrument employing a Shack-Hartmann wavefront sensor injects near infrared light into a patient's eye which focuses on the retina and scatters back toward the instrument. This light is imaged onto the Shack-Hartmann lenslet array, and each lenslet in the lenslet array focuses the local portion of the incident light it intercepts onto the detector array, as described above. Data ("wavefront data") pertaining to the locations of the light spots is used to derive slope information using a least squares fit method, and thereby to construct the wavefront of the received light.

The nominally rectilinear array of light spots is produced by a rectilinear lenslet array. The detailed analysis of the locations of these light spots relative to their reference locations (i.e., the locations that result when a true plane wave is applied to the lenslet array) yields the local gradient of the incident wavefront. The overall area in which focal spots are present is determined by the patient's pupil, and analysis of this illuminated area yields the location size and shape of the pupil.

The application of Shack-Hartmann wavefront sensors to ophthalmic aberrometry has been a success.

However, the quality of the fit wavefront data, usually evaluated using Zernike coefficients, is affected by the quality of the light spot location data, and therefore it is important to ensure that the data quality is adequate to the measurement accuracy and precision requirements.

In particular, if the wavefront is not isoplanatic, the quality of the light spots erodes rapidly and it becomes more difficult to determine the locations of the light spots. More specifically, measuring highly aberrated light beams can lead to focal spot crossover such that light spot from a particular lenslets end up in locations on the pixel array that lie under neighboring lenslets, or end up in irregular locations not defined by a grid. As explained above with respect to FIGS. 4A-4C, in a traditional system the first step to locating the light spots is to search in a predefined Area of Interest (AOI). However with a highly aberrated beam, such as would typically be produced by light passing through a diffractive region of an implanted combined diffractive-refractive intraocular lens, there could be more than one light spot in an AOI, or an AOI for a particular pixel may include part of a light spot for a neighboring pixel. This will lead to errors in these traditional light spot location algorithms.

On method of dealing with this problem is the inclusion of a dynamic range limiting aperture in the measurement instrument to prevent to prevent light spots from appearing outside their AOIs on the detector array, as described for example in U.S. Pat. No. 6,550,917 issued on 22 Apr. 2003 to Daniel R. Neal et al., which is hereby incorporated by reference for all purposes as if fully set forth herein. The dynamic range limiting aperture clips portions of the light beam that impinge on the detector array above a certain angle. Accordingly, the dynamic range limiting aperture limits the dynamic range of the measurement instrument. So other methods of handling highly aberrated wavefronts are desired.

In addition to the problem of determining the locations of light spots fora highly aberrated light beam, in some cases lenslet array 310 may not be perfectly aligned with the pixels of detector array 320. That is, there may be a translational offset and/or a rotation angle between lenslet array 310 and detector array 320 that may complicate the wavefront analysis.

Additionally, there is a problem of determining what constitutes a valid light spot on the detector array, especially in the case of a highly aberrated wavefront.

Techniques for addressing some or all of these issues are disclosed in U.S. Pat. No. 7,988,293 issued on 2 Aug. 2011 to Thomas D. Raymond et al., which is hereby incorporated by reference for all purposes as if fully set forth herein.

Figure 5:
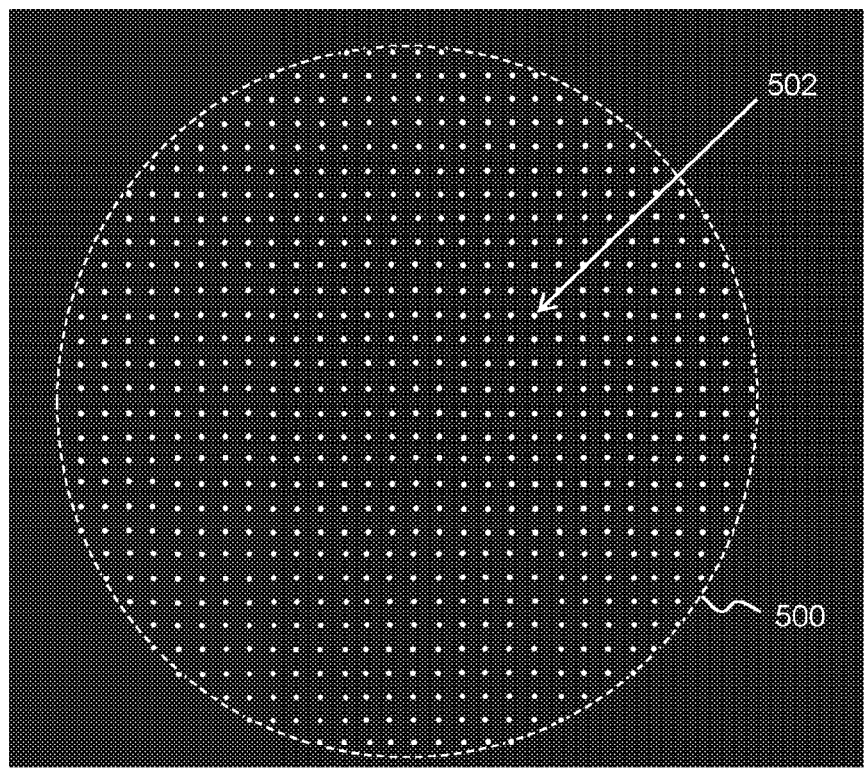
FIG. 5 illustrates light spots produced by imaging a planar wavefront of interest onto a detector array of a wavefront sensor through an eye which does not have implanted combined diffractive-refractive IOL.

FIG. 5 illustrates light spots 502 produced by imaging a planar wavefront of light onto a detector array 500 of a wavefront sensor through an eye which does not have implanted combined diffractive-refractive IOL. As seen in FIG. 5, light spots 502 are well formed and evenly distributed across detector array, making it relatively easy for a processor which receives wavefront data from detector array 500 to determine which light spots are valid and belong to which lenslet of the lenslet array which imaged the light onto detector array, and thereby calculate the wavefront and, in case of light returning from an eye, determine optical characteristics of the eye (such as its refraction), as discussed above.

However when light returning from an eye with an implanted combined diffractive-refractive IOL onto a detector array of a wavefront sensor, the situation is quite different. The presence of one or more diffractive regions in the combined diffractive-refractive IOL may cause the returning light which passes through those regions to become very non-planar and highly aberrated. In that case, as discussed above, the light spots imaged onto the detector array from that portion of the returning light end up in irregular locations not defined by a grid and in fact may be quite distorted or smeared.

In particular, when a Shack-Hartmann wavefront sensor is employed to measure an eye in which a combined diffractive-refractive IOL is implanted, light which returns from the diffractive structure of the IOL produces light spot patterns that are distorted and difficult to analyze correctly. Where a diffractive ring passes through a location that corresponds to an individual lenslet of the lenslet array of the Shack-Hartmann wavefront sensor, the light spot that s formed underneath that lenslet will be smeared out compared to the shape it would have had if no diffractive ring had intersected it. The amount of smearing is enough to affect accuracy of the measurements but it may not be enough to make it easy to identify and disregard focal spots based only on how smeared they appear, for example using techniques disclosed in U.S. Pat. No. 7,988,293, cited above. One reason for this is that variations in focal spot smearing are often seen across the field of view of a Shack-Hartmann wavefront sensor even when purely refractive IOLs are implanted. Also, some variation of apparent smearing of the spots is caused by the fact that each focal spot is sampled somewhat coarsely by the pixels or detectors in the detector array, and how a particular light spot happens to land on the pixel grid.

Figure 6:
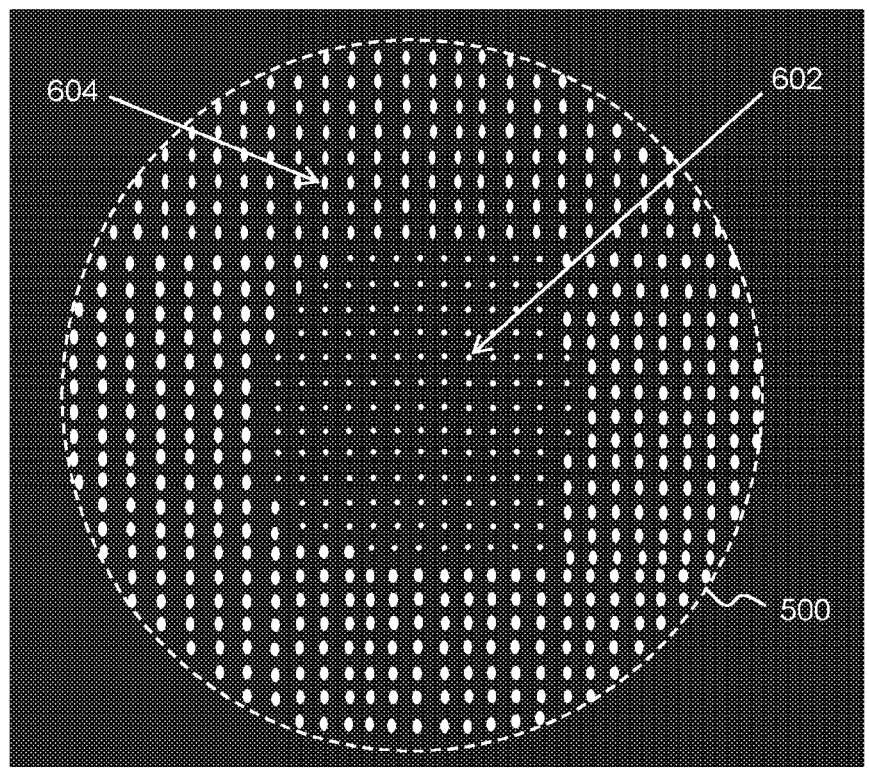
FIG. 6 illustrates an example of light spots produced by imaging light passing through an eye with an implanted combined diffractive-refractive IOL onto a detector array of a wavefront sensor.

FIG. 6 illustrates an example of light spots produced by imaging light passing through an eye with an implanted combined diffractive-refractive IOL onto detector array 500 of a wavefront sensor. Here, it can be seen that there are at least two sets of light spots: a first set of light spots 602 which returned from the retina through the refractive region of the combined diffractive-refractive intraocular lens, and a second set of light spots 604 which returned from the retina through at least one diffractive region of the combined diffractive-refractive intraocular lens. In FIG. 6, the distortion and smearing of light spots 604 may be exaggerated for emphasis and ease of illustration. In many cases, the distortion and smearing of light spots 604 may be less than that illustrated in FIG. 6. In some cases, the distortion and smearing of light spots 604 may be greater than that illustrated in FIG. 6.

Significantly, FIG. 6 illustrates the presence of the first set of light spots 602 which returned from the retina through a refractive region of the combined diffractive-refractive intraocular lens and which are not distorted by the diffractive rings or diffractive regions of the combined diffractive-refractive intraocular lens. The inventors have recognized that the wavefront data from detector array 500 produced in response to the first set of light spots 602 (i.e., excluding wavefront or detector data produced from the second set of light spots 604) may be processed by a processor using normal wavefront calculation algorithms to reconstruct the wavefront and thereby ascertain or determine the refraction of the eye into which the combined diffractive-refractive intraocular lens is implanted.

More specifically, for example, certain combined diffractive-refractive IOLs, such as combined diffractive-refractive IOL 20 of FIGS. 2A-3B, have a central refractive zone or region (e.g., refractive region 21 in FIGS. 2A-2B), which may be slightly larger than 1 mm in diameter, that is free from diffractive rings. In some designs the central refractive region has a power that matches the distant refractive power of the IOL. In other cases the base refraction may be offset from the power of the central refractive region by an amount known from the design so measurement of the central refractive region enables determination of the base power. In still other combined diffractive-refractive IOLs, the refractive region may not be in the center of the IOL, but may be, for example, and annular zone or region around the central zone or region.

The solution is to identify a region or area of the wavefront detector which receives light spots 602 from the refractive region (e.g., refractive region 21) of the combined diffractive-refractive intraocular lens (e.g., combined diffractive-refractive IOL 20), and then use the wavefront data from that region of the wavefront detector to calculate the base refraction of the eye.

Figure 7:
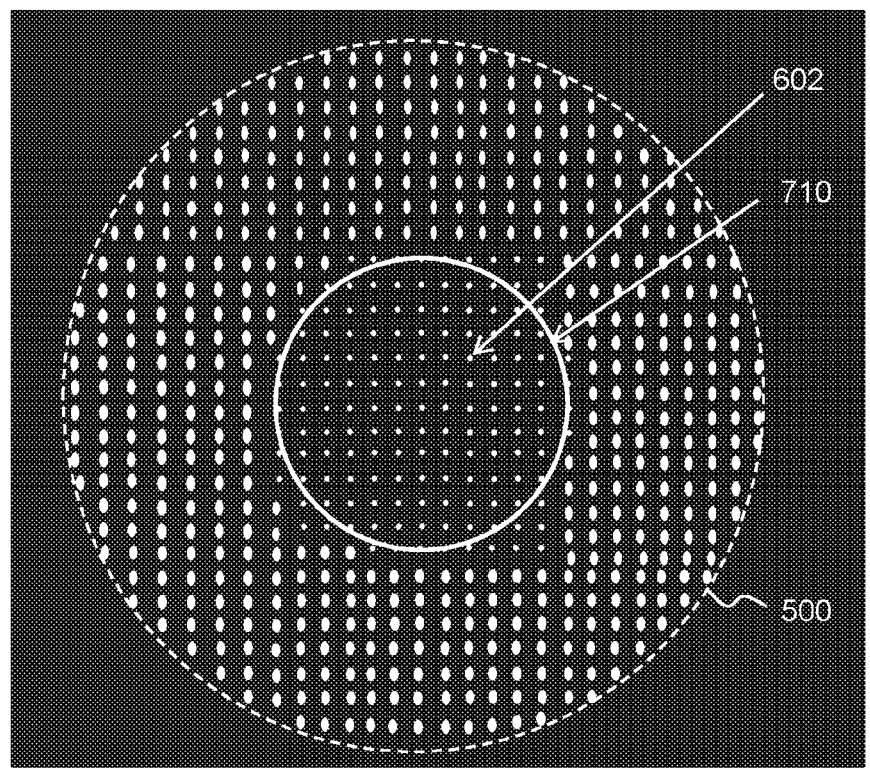
FIG. 7 illustrates a region of valid light spots on a detector array of a wavefront sensor for making a refraction measurement of an eye having an implanted combined diffractive-refractive IOL.

FIG. 7 illustrates a first region 710 of valid light spots 602 on detector array 500 of a wavefront sensor for making a refraction measurement of an eye having an implanted combined diffractive-refractive IOL.

Here, it is not required or important to select first region 710 to include all of the light spots 602. Instead, first region 710 of detector array 500 should be selected to include at least some of the first set of light spots 702 returned from the retina through the refractive region of the combined diffractive-refractive intraocular lens, and which exclude the second set of light spots 804 returned from the retina through the diffractive region(s) of the combined diffractive-refractive intraocular lens.

In some embodiments, the first region may be selected by: displaying to a user a first real-time image of the eye, including the combined diffractive-refractive intraocular lens implanted therein, on an iris camera display; displaying to the user a second real-time image of the first and second sets of light spots on the detector array at a same time as displaying the first real-time image, and receiving from the user a selection of the first region in response to viewing the first and second real-time images.

In many cases, diffractive ring features of the combined diffractive-refractive IOL can be seen in retro-illuminated images taken by the iris camera. Accordingly, in some embodiments, the user finds first region 710 by finding the diffractive ring features in the iris camera image and then matches those features to the illuminated region of the wavefront image to identify the refractive region of the combined diffractive-refractive IOL. Other forms of illumination may enhance the images further.

If the eye is dilated to make a measurement, features near the edge of the combined diffractive-refractive IOL may be revealed. These include toric alignment marks for aligning the angular orientation of the combined diffractive-refractive IOL within the eye. In some embodiments, these features may also be employed by a user to identify tile exact center of the combined diffractive-refractive IOL and the refractive region of the combined diffractive-refractive IOL so that first region 710 may be chosen.

In other embodiments, a processor receives wavefront data from the detectors of detector array 500 and processes the wavefront data to select first region 710. That is, the processor receives first set of wavefront data from the first set of light spots 602 produced from light which returned from the retina of the eye through the refractive region of the combined diffractive-refractive IOL within the eye, and a second set of wavefront data in response to the second set of light spots 604 produced from light which returned from the retina through the diffractive region(s) of the combined diffractive-refractive intraocular lens, and the processor processes the first and second sets of wavefront data to select first region 710.

Figure 8:
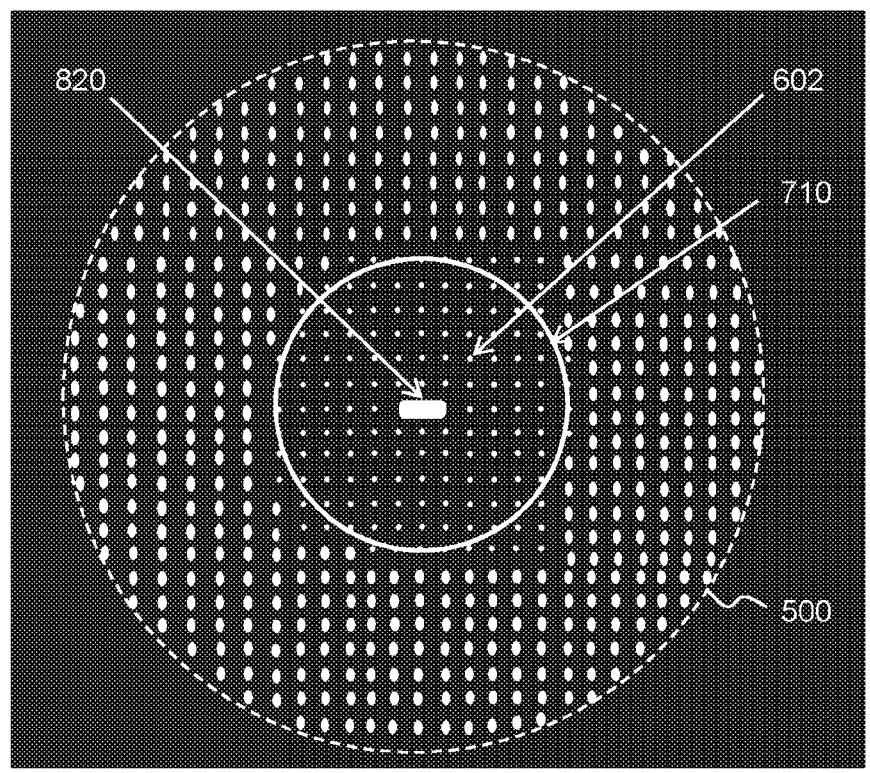
FIG. 8 illustrates light spots produced by imaging light passing through an eye with an implanted combined diffractive-refractive IOL onto a detector array of a wavefront sensor, together with corneal reflex.

FIG. 8 illustrates light spots produced by imaging light passing through an eye with an implanted combined diffractive-refractive IOL onto a detector array of a wavefront sensor, together with a so-called "corneal reflex."

As illustrated in FIG. 8, the incident near-infrared probe beam not only scatters from a patient's retina, but also reflects directly from the combined diffractive-refractive intraocular lens which is implanted on the eye. The use of a Range Limiting Aperture (RLA) in the measurement instrument, as described in greater detail below, can significantly reduce the intensity of the reflected light. However, this so-called "corneal reflex" 820 is generally orders of magnitude brighter than the desired retinally scattered light and should be excluded from the wavefront calculations. Indeed, as is illustrated in FIG. 8, corneal reflex 820 can affect a neighborhood of nearby light spots 602 by introducing stray light that can alter the true light spot location or mask the light spot entirely. For these reasons, the qualification and/or exclusion of wavefront data from light spots in and around the corneal reflex can be challenging.

Accordingly, in some embodiments, to avoid having corneal reflex 820 appear in first region 710, one or more aids are provided to help the instrument operator align the measurement instrument so that corneal reflections of the probe beam do not obscure first region 710 including light spots 602 from the refractive region (e.g., central portion) of the combined diffractive-refractive IOL.

Figure 9:
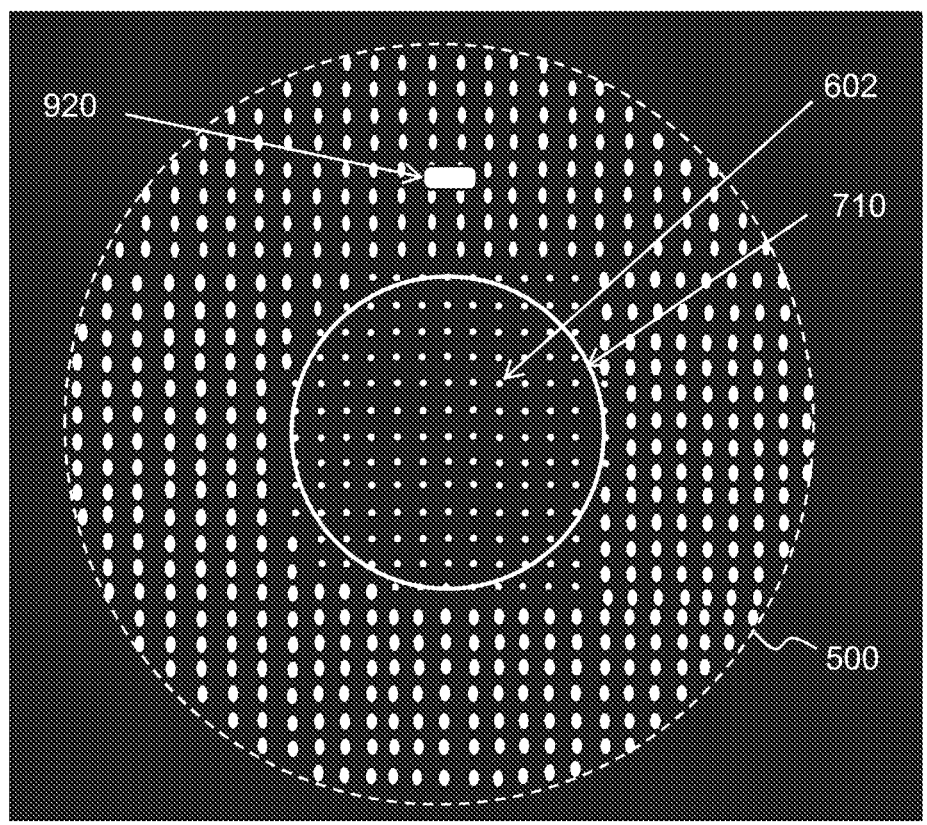
FIG. 9 illustrates light spots produced by imaging light passing through an eye with an implanted combined diffractive-refractive IOL onto a detector array of a wavefront sensor, together with corneal reflex whose location has been moved by supplying the probe beam to the eye at an offset from the center of the eye.

FIG. 9 illustrates light spots 602 produced by imaging light passing through an eye with an implanted combined refractive-diffractive IOL onto detector array 500 of a wavefront sensor, together with a corneal reflex 920 whose location has been moved by supplying the probe beam to the eye at an offset from the center of the eye and outside of first region 710.

In some embodiments, a measurement instrument displays a first real-time image of the eye, including the combined diffractive-refractive intraocular lens implanted therein, to an operator or user on an iris camera display, and at the same time display a second real-time image of the first and second sets of light spots on the detector array to the user. The system then receives from the user a selection of the offset for the probe beam in response to viewing the first and second real-time images. In some embodiments, the user may manually adjust the offset, for example through a joystick. In other cases, the selection of the offset may be made through a user interface (e.g., a graphical user interface) of the Because the corneal reflex is so bright, the probe beam level could low, for example two microwatts, and the corneal reflex would show up on the display if it were going to occur. During the wavefront sensor measurement, the probe beam light level would be set to normal, typically forty microwatts.

In some embodiments, as described in greater detail below, the measurement instrument may include an offset device configured to cause the probe beam to pass through the combined diffractive-refractive intraocular lens to the retina of the eye offset from a center of the combined diffractive-refractive intraocular lens such that a corneal reflection from the eye does not appear in first region 710 of detector array 500. The instrument may also include a processor which is configured to: receive a first set of wavefront data in response to the first set of light spots 602 on detector array 500 which returned from the retina through the at least one diffractive region of the combined diffractive-refractive intraocular lens, and a second set of wavefront data in response to the second set of light spots 604 on detector array 500 which returned from the retina through the diffractive region(s) of the combined diffractive-refractive intraocular lens; process the first and second sets of wavefront data to detect corneal reflex 820 in the returned light; and control the offset device to cause the probe beam to pass through the combined diffractive-refractive intraocular lens such that corneal reflex 820 is not located in first region 710.

In some embodiments, the offset device comprises: an optical element having an input surface which is configured to receive the probe beam at a non-zero angle with respect to a normal to the input surface; and a solenoid controlled by the processor to tilt the optical element to change the non-zero angle such that the probe beam passes through the refractive region of the combined diffractive-refractive intraocular lens to the retina of the eye offset from the center of the combined diffractive-refractive intraocular lens such that corneal reflex 820 does not appear in first region 710.

In some embodiments, the processor may automatically cause the probe beam to automatically move into two or three different lateral locations, spaced apart for example by 1.5 mm. This shift would ensure that there would be at least one image where there was no obscuring corneal reflection in first region 710.

In some embodiments, the offset device comprises a movable stage to which the light source, detector array, light spot generator, and at least a portion of the optics are mounted, and the processor is configured to control movement of the movable stage with respect to the eye such that the probe beam passes through the combined diffractive-refractive intraocular lens to the retina of the eye offset from the center of the combined diffractive-refractive intraocular lens such that corneal reflex 820 does not appear in first region 710.

Figure 10:
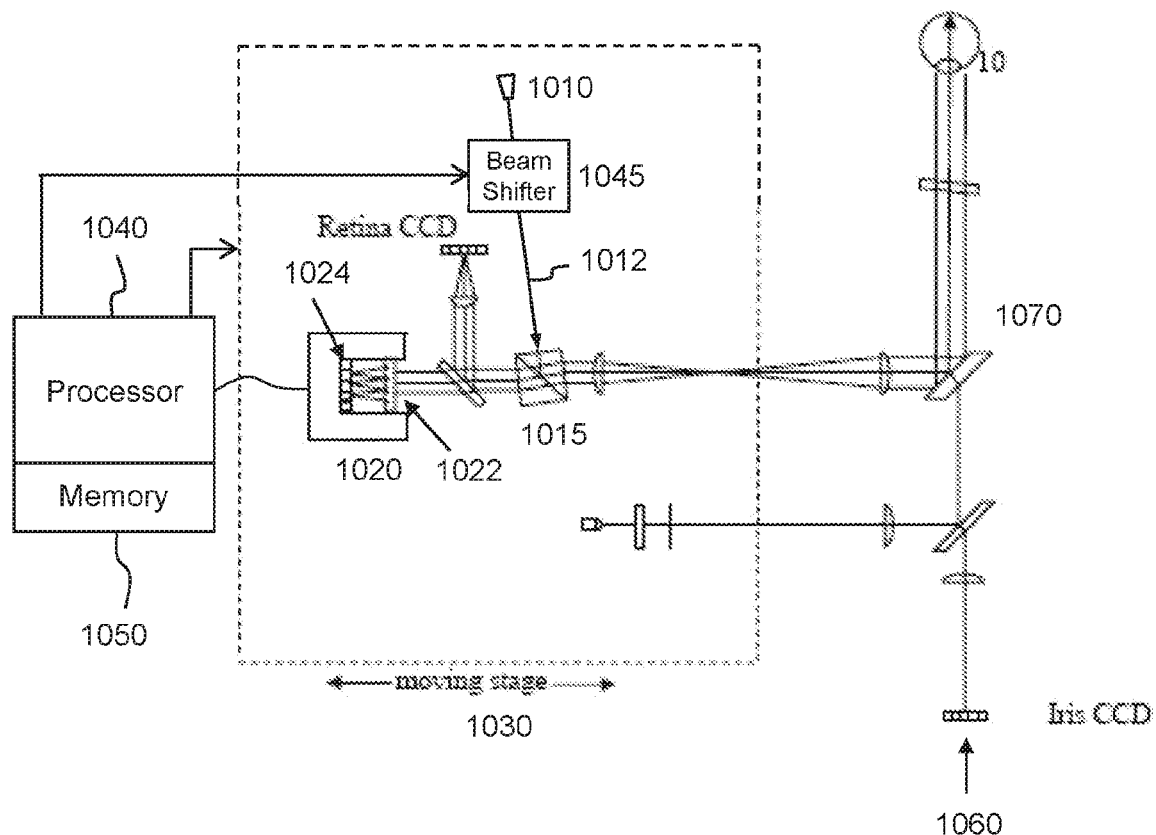
FIG. 10 illustrates an embodiment of a measurement instrument employing a wavefront sensor.

FIG. 10 illustrates an embodiment of a measurement instrument employing a wavefront sensor. In particular, FIG. 10 illustrates a wavefront aberrometer 1000 for making wavefront measurements of a subject's eye 10. Among other components, wavefront aberrometer 1000 includes a light source 1010, a wavefront sensor 1020, and other components on a moving stage 1030, a processor 1040, memory 1050 associated with the processor 1040, and an iris camera 1060. Further details of the construction and operation of wavefront aberrometer 1000 can be found in U.S. Pat. No. 7,494,220 issued on 24 Feb. 2009 in the names of Richard Copland et al., the entirety of which is hereby incorporated herein by reference for all purposes as if fully set forth herein.

Of particular relevance here, wavefront sensor 1020 operates in conjunction with processor 1040 and associated memory 1050 to perform wavefront measurements on eye 10. Wavefront sensor 1020 includes a lenslet array 1022 and a detector array (also known as a "pixel array") 1024. Further details of the construction and operation of lenslet array 1022 and detector array 1024 may be understood with reference to the description of Shack-Hartmann wavefront sensor 300 of FIG. 3 provided above. Wavefront data from detector array 1024 is supplied to processor 1040 and associated memory 1050 to execute one or more algorithms to determine a wavefront of a light beam received from the eye 10. Beneficially, processor 1040 may perform these algorithms in accordance with instructions stored in memory 1050.

Beneficially, processor 1040 executes an algorithm to measure the refraction of an eye which has a combined diffractive-refractive IOL implanted therein, as discussed above and further discussed below with respect to FIG. 11.

Wavefront aberrometer 1000 also includes an offset device 1045 disposed in an optical path between light source 1010 and optical beam splitters 1015 and 1070. Offset device 1045 may operate under control of processor 1040 as described above with respect to FIGS. 8 and 9 to provide an offset to the probe beam 1012 to cause any corneal reflex to appear outside a first region of detector array 1024 where a first set of light spots appear which returned from the retina through the refractive region of the combined diffractive-refractive intraocular lens which is implanted into eye 10.

Figure 11:
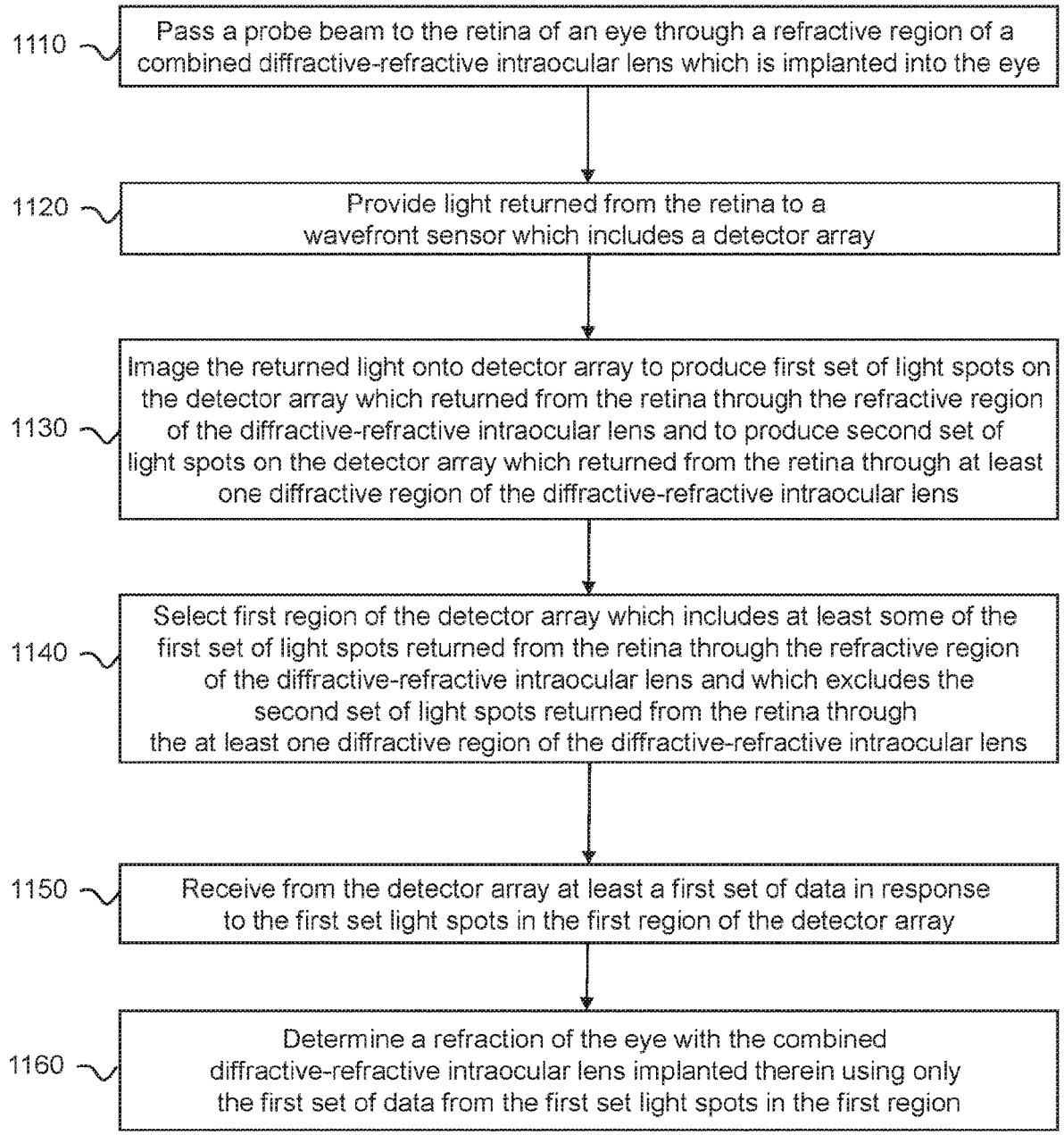
FIG. 11 is a flowchart of a method of making an optical measurement of an eye with an implanted combined diffractive-refractive IOL.

FIG. 11 shows a flowchart illustrating one embodiment of a method 1100 of measure the refraction of an eye which has a combined diffractive-refractive IOL implanted therein. Beneficially, in one embodiment method 1100 may be performed by wavefront aberrometer 1000 under control of processor 1040. Accordingly, to provide a more concrete explanation, method 1100 will be described below with respect to wavefront aberrometer 1000. However, it should be understood that in general method 1200 may be performed by devices other than wavefront aberrometers having different configurations than wavefront aberrometer 1000.

In an act 1110, wavefront aberrometer 1000 passes a probe beam to the retina of eye 10 through a refractive region of a combined diffractive-refractive intraocular lens which is implanted into eye 10.

In an act 1120, wavefront aberrometer 1000 provides light returned from the retina to a wavefront sensor 1020 which includes a detector array 1024.

In an act 1130, lenslet array 1022 images the returned light from the eye onto detector array 1024 to produce first set of light spots which returned from the retina through the refractive region of the combined diffractive-refractive intraocular lens, and to produce second set of light spots which returned from the retina through at least one diffractive region of the combined diffractive-refractive intraocular lens.

In an act 1140, a first region of detector array 1024 is selected which includes at least some of the first set of light spots returned from the retina through the refractive region of the combined diffractive-refractive intraocular lens and which excludes the second set of light spots returned from the retina through the at least one diffractive region of the combined diffractive-refractive intraocular lens.

In an act 1150, processor 1040 receives from detector array 1024 at least a first set of data in response to the first set light spots in the first region of detector array 1024.

In an act 1160, processor 1040 determines a refraction of eye 10 with the combined diffractive-refractive intraocular lens implanted therein using only the first set of data from the first set light spots in the first region of detector array 1024.

Figure 12:
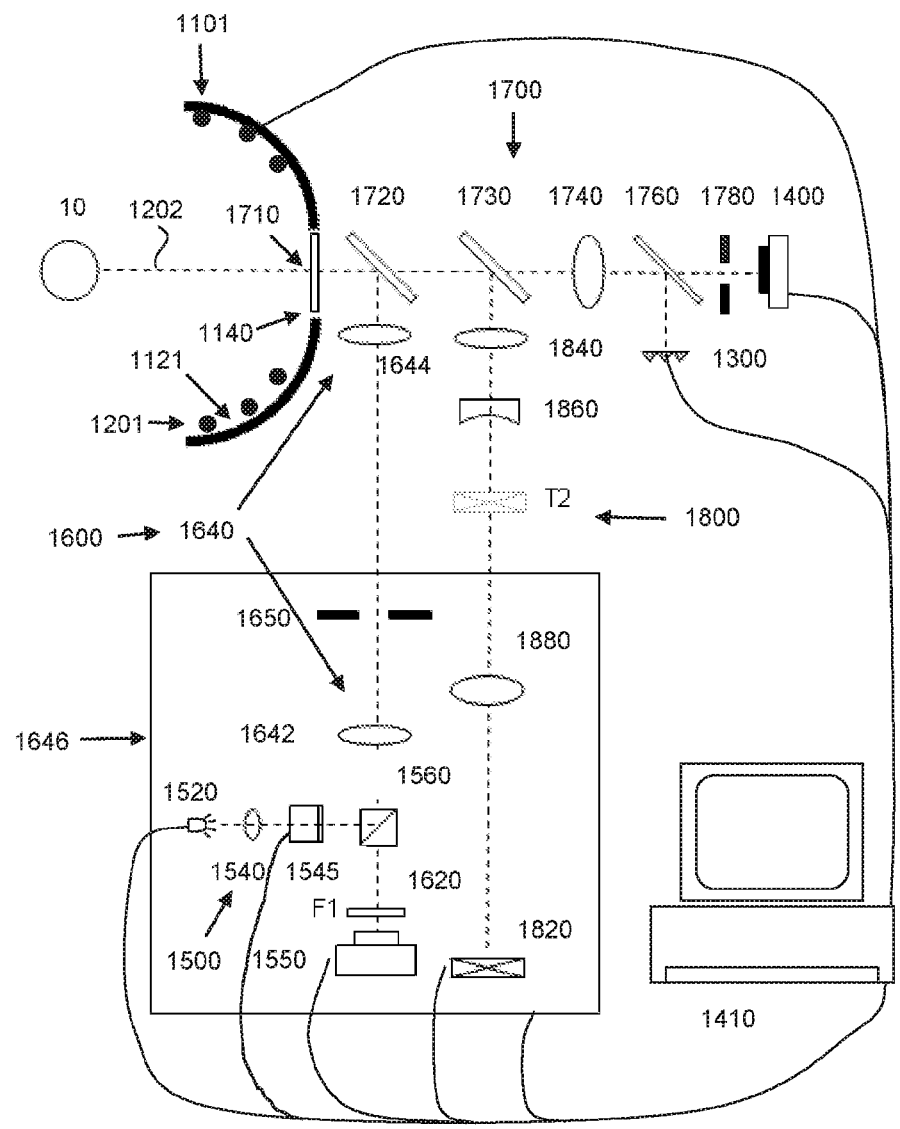
FIG. 12 illustrates one embodiment of a system for measuring wavefront aberrations and corneal topography of an eye.

FIG. 12 shows one embodiment of a system 1200 for measuring aberrations and the corneal topography of an eye 10. System 1200 comprises a structure 1101 having a principal surface 1121 with an opening or aperture 1140 therein; a plurality of first (or peripheral) light sources 1201 provided on the principal surface 1121 of the structure 1101; a plurality of second, or central, light sources 1300 (also sometimes referred to as "Helmholtz light sources"); a detector array 1400; a processor 1410; a third light source 1500 providing a probe beam; a wavefront sensor 1550; and an optical system 1700 disposed along a central axis 1102 passing through the opening or aperture 1140 of the structure 1101. Optical system 1700 comprises a quarterwave plate 1710, a first beamsplitter 1720, a second beamsplitter 1730, an optical element (e.g., a lens) 1740, a third beamsplitter 1760, and a structure including an aperture 1780.

Beneficially, third light source 1500 includes a lamp 1520, a collimating lens 1540, and light source polarizing beamsplitter 1560. Associated with third light source 1500 and wavefront sensor 1550 in a wavefront analysis system 1600 also comprising: a polarizing beamsplitter 1620; an adjustable telescope 1640 comprising a first optical element (e.g., lens) 1642 and a second optical element (e.g., lens) 1644 and a movable stage or platform 1646; and a dynamic-range limiting aperture 1650 for limiting a dynamic range of light provided to wavefront sensor 1550. It will be appreciated by those of skill in the art that the lenses 1642, 1644, or any of the other lenses discussed herein, may be replaced or supplemented by another type of converging or diverging optical element, such as a diffractive optical element.

Beneficially, system 1200 includes offset element 1545 disposed in an optical path between lamp 1520 and light source polarizing beamsplitter 1560.

Beneficially, system 1200 further comprises a fixation target system 1800, comprising light source 1820 and lenses 1840, 1860, and 1880.

Further details of system 1200 can be found by reference to U.S. Patent Application Publication 2009/0002631, filed in the names of Charles E. Campbell et al., and published on 1 Jan. 2009, the entirety of which is hereby incorporated herein by reference for all purposes as if fully set forth herein.

The operation of the topographer portion of system 1200 may be illustrated based on the combined use of first and second light sources 1201, 1300. In general, the images of first light sources 1201 that appear on detector array 1400 emanate from an outer region of the surface of the cornea, and the images of second light sources 1300 that appear on detector array 1400 emanate from a central or paraxial region of the surface of the cornea. Accordingly, even though information about the central region of the corneal surface (e.g., surface curvature) cannot be determined from the images of first light sources 1201 on detector array 1400, such information can be determined from the images of second light sources 1300 on detector array 1400.

Detector array 1400 detects the light spots projected thereon from both second light sources 1300 (detected at a central portion of detector array 1400) and first light sources 1201 (detected at a peripheral portion of detector array 1400) and provides corresponding output signals to processor 1410. Processor 1410 determines the locations and/or shapes of the light spots on detector array 1400, and compares these locations and/or shapes to those expected based for a standard or model cornea, thereby allowing processor 1410 to determine the corneal topography of eye 10. Accordingly, the topography of the entire corneal surface can be characterized by system 1200 without a "hole" or missing data from the central corneal region.

Beneficially, processor 1410 executes an algorithm to measure the refraction of an eye which has a combined diffractive-refractive IOL implanted therein, as discussed above with respect to FIGS. 7-10.

Although system 1200 combines the a corneal topographer and a wavefront aberrometer in a single optical measurement instrument, other optical measurement instruments may combine a corneal topographer, a wavefront aberrometer, and an optical coherence topographer, and these other optical measurement instruments may also be configured to measure the refraction of an eye which has a combined diffractive-refractive IOL implanted therein using techniques described above with respect to FIGS. 7-11.

Figure 13:
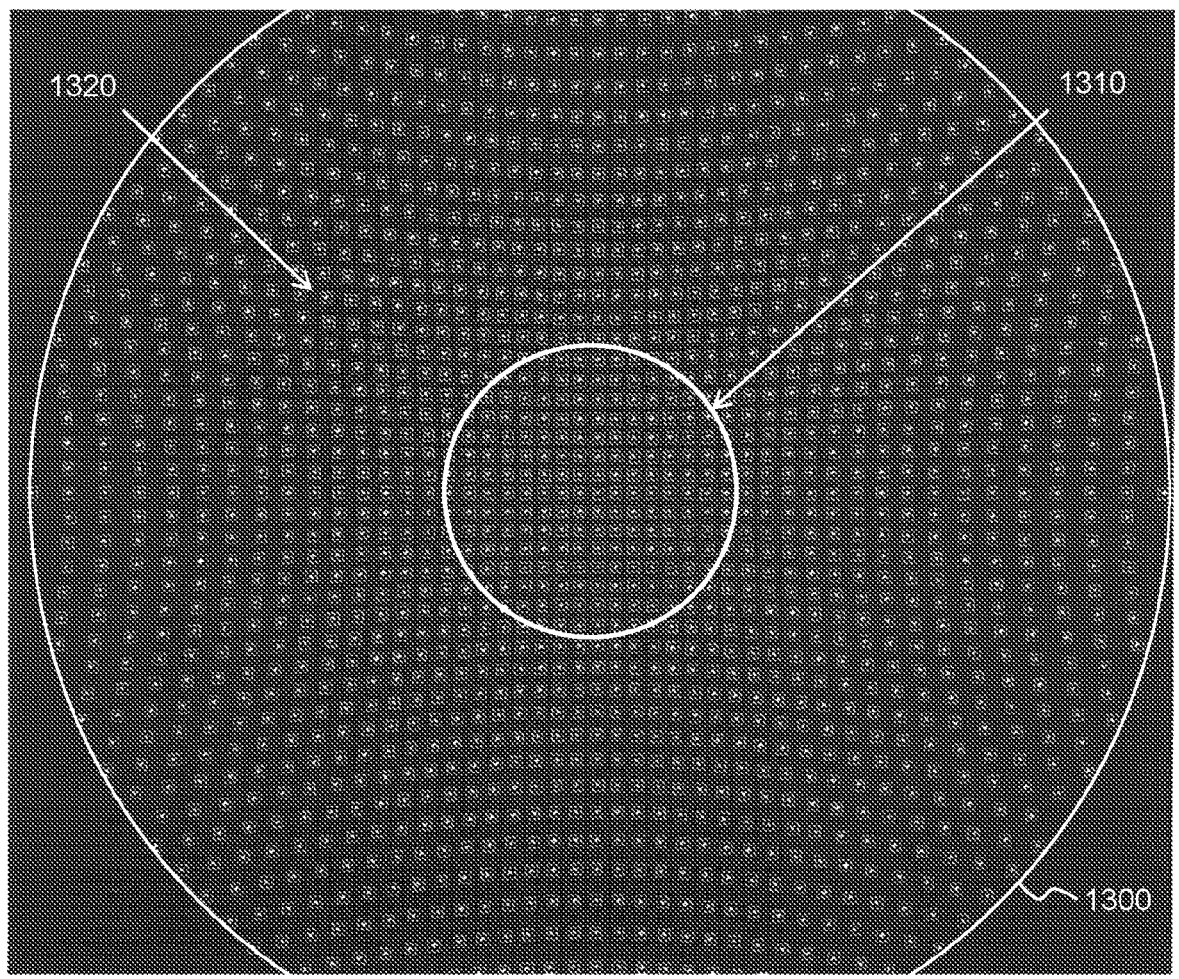
FIG. 13 illustrates light spots produced by imaging a planar wavefront of interest onto a detector array of a wavefront sensor which has smaller lenslets in a central region than in more peripheral regions.

FIG. 13 illustrates light spots produced by imaging a planar wavefront of interest onto a detector array 1300 of a wavefront sensor which has smaller lenslets in a central region 1310 than in more peripheral regions 1320 (i.e., the density of lenslets in central region 1310 is greater than in peripheral region(s) 1320). In some embodiments, the density of detector elements in central region 1310 is also greater than in peripheral region(s) 1320. In some embodiments, a system such as system 1200 or a wavefront aberrometer such as wavefront aberrometer 1000 may employ a wavefront sensor such as that illustrated in FIG. 13, which may allow the wavefront aberrometer to obtain more data from a central region of an eye for calculating the wavefront of light returning from the eye. This may be especially beneficial when the eye has an implanted combined diffractive-refractive intraocular lens which has a central refractive region, such as combined diffractive-refractive intraocular lens 20 described above with respect to FIGS. 2A-2B.

While preferred embodiments are disclosed herein, many variations are possible which remain within the concept and scope of the invention. Such variations would become clear to one of ordinary skill in the art after inspection of the specification, drawings and claims herein. The invention therefore is not to be restricted except within the spirit and scope of the appended claims.

We claim:

1. A method, comprising:
   passing a probe beam to a retina of an eye through a combined diffractive-refractive intraocular lens which is implanted into the eye;
   providing light returned from the retina to a wavefront sensor which includes a detector array;
   the wavefront sensor imaging the returned light onto the detector array to produce a first set of light spots on the detector array which returned from the retina through a refractive region of the combined diffractive-refractive intraocular lens, and to produce a second set of light spots on the detector array which returned from the retina through at least one diffractive region of the combined diffractive-refractive intraocular lens;
   selecting a first region of the detector array which includes at least some of the first set of light spots returned from the retina through the refractive region of the combined diffractive-refractive intraocular lens and which excludes the second set of light spots returned from the retina through the at least one diffractive region of the combined diffractive-refractive intraocular lens;
   a processor receiving from the detector array at least a first set of wavefront data in response to the first set light spots in the first region of the detector array; and
   the processor determining a refraction of the eye with the combined diffractive-refractive intraocular lens implanted therein using only the first set of wavefront data from the first set light spots in the first region.

2. The method of claim 1, further comprising:
   displaying to a user a first real-time image of the eye, including the combined diffractive-refractive intraocular lens implanted therein, on an iris camera display;
   displaying to the user a second real-time image of the first and second sets of light spots on the detector array at a same time as displaying the first real-time image; and
   receiving from the user a selection of the first region in response to viewing the first and second real-time images.

3. The method of claim 2, wherein the user identifies the first set of light spots returned from the retina through the refractive region of the combined diffractive-refractive intraocular lens by viewing diffractive ring features in the first real-time image.

4. The method of claim 2, wherein the user identifies the first set of light spots returned from the retina through the refractive region of the combined diffractive-refractive intraocular lens by viewing toric alignment marks of the combined diffractive-refractive intraocular lens on the iris camera display.

5. The method of claim 1, wherein the processor also receives a second set of wavefront data in response to the second set of light spots on the detector array which returned from the retina through the at least one diffractive region of the combined diffractive-refractive intraocular lens, the processor processing the first and second sets of wavefront data to select the first region.

6. The method of claim 1, comprising passing the probe beam through the refractive region of the combined diffractive-refractive intraocular lens to the retina of the eye offset from a center of the combined diffractive-refractive intraocular lens such that a corneal reflection from the eye does not appear in the first region of the detector array.

7. The method of claim 6, wherein the processor also receives a second set of wavefront data in response to the second set of light spots on the detector array which returned from the retina through the at least one diffractive region of the combined diffractive-refractive intraocular lens, the processor processing the first and second sets of wavefront data to detect a corneal reflex in the returned light and controlling the offset at which the probe beam passes through the combined diffractive-refractive intraocular lens such that the corneal reflex is not located in the first region.

8. The method of claim 6, further comprising:
   displaying to a user a first real-time image of the eye, including the combined diffractive-refractive intraocular lens implanted therein, on an iris camera display;
   displaying to the user a second real-time image of the first and second sets of light spots on the detector array at a same time as displaying the first real-time image; and
   receiving from the user a selection of the offset in response to viewing the first and second real-time images.

9. A device, comprising:
   a light source configured to produce a probe beam;
   optics configured to pass the probe beam to a retina of an eye through a combined diffractive-refractive intraocular lens which is implanted into the eye;
   a detector array;
   a light spot generator adapted to receive light returned from the retina and in response thereto to produce on the detector array a first set of light spots which returned from the retina through a refractive region of the combined diffractive-refractive intraocular lens and a second set of light spots on the detector array which returned from the retina through at least one diffractive region of the combined diffractive-refractive intraocular lens; and
   a processor configured to:
      receive from the detector array at least a first set of wavefront data in response to a first set light spots in a first region of the detector array returned from the retina through the refractive region of the combined diffractive-refractive intraocular lens, wherein the first region excludes the second set of light spots returned from the retina through the at least one diffractive region of the combined diffractive-refractive intraocular lens, and
      determine a refraction of the eye with the combined diffractive-refractive intraocular lens implanted therein using only the first set of wavefront data from the first set light spots in the first region.

10. The device of claim 9, further comprising at least one display configured to:
    display to a user a first real-time image of the eye, including the combined diffractive-refractive intraocular lens implanted therein, on an iris camera display; and
    display to the user a second real-time image of the first and second sets of light spots on the detector array at a same time as displaying the first real-time image, and
    wherein the device is configured to receive from the user a selection of the first region in response to viewing the first and second real-time images.

11. The device of claim 10, wherein the at least one display is configured to display diffractive ring features in the first real-time image.

12. The device of claim 10, wherein the at least one display is configured to display toric alignment marks of the combined diffractive-refractive intraocular lens.

13. The device of claim 9, wherein the processor is also configured to receive a second set of wavefront data in response to the second set of light spots on the detector array which returned from the retina through the at least one diffractive region of the combined diffractive-refractive intraocular lens, the processor being further configured to process the first and second sets of wavefront data to select the first region.

14. The device of claim 9, wherein the optics comprises an offset device configured to cause the probe beam to pass through the refractive region of the combined diffractive-refractive intraocular lens to the retina of the eye offset from a center of the combined diffractive-refractive intraocular lens such that a corneal reflection from the eye does not appear in the first region of the detector array.

15. The device of claim 14, wherein the processor is also configured to:
receive a second set of wavefront data in response to the second set of light spots on the detector array which returned from the retina through the at least one diffractive region of the combined diffractive-refractive intraocular lens;
process the first and second sets of wavefront data to detect a corneal reflex in the returned light; and
control the offset device to cause the probe beam to pass through the combined diffractive-refractive intraocular lens such that the corneal reflex is not located in the first region.

16. The device of claim 15, wherein the offset device comprises:
an optical element having an input surface which is configured to receive the probe beam at a non-zero angle with respect to a normal to the input surface; and
a solenoid controlled by the processor to tilt the optical element to change the non-zero angle such that the probe beam passes through the refractive region of the combined diffractive-refractive intraocular lens to the retina of the eye offset from the center of the combined diffractive-refractive intraocular lens.

17. The device of claim 15, wherein the offset device comprises a movable stage to which the light source, detector array, light spot generator, and at least a portion of the optics are mounted, and wherein the processor is configured to control movement of the movable stage with respect to the eye such that the probe beam passes through the refractive region of the combined diffractive-refractive intraocular lens to the retina of the eye offset from the center of the combined diffractive-refractive intraocular lens.

18. The device of claim 9, wherein the light spot generator comprises an array of lenslets, wherein lenslets of the array which are located in a central region of the array are smaller than lenslets of the array which are located in a peripheral region of the array.

* * * * *